United States Patent
Ismer et al.

(10) Patent No.: US 8,355,781 B2
(45) Date of Patent: Jan. 15, 2013

(54) BIVENTRICULAR HEART STIMULATOR

(75) Inventors: Bruno Ismer, Rostock (DE); Thomas Koerber, Rostock (DE); Wolfgang Voss, Kritzmow (DE); Georg Heinrich von Knorre, Rostock (DE); Bjoern Riedel, Rostock (DE); Andreas Neumann, Berlin (DE); Ulrich Busch, Berlin (DE); Juergen Pilz, Berlin (DE); Thomas Brueggemann, Berlin (DE); Ralf Peters, Neuenkirchen (DE)

(73) Assignee: Biotronik CRM Patent AG, Baar (CH)

( * ) Notice: Subject to any disclaimer, the term of this patent is extended or adjusted under 35 U.S.C. 154(b) by 736 days.

(21) Appl. No.: 12/271,908

(22) Filed: Nov. 16, 2008

(65) Prior Publication Data

US 2009/0163967 A1 Jun. 25, 2009

(30) Foreign Application Priority Data

Dec. 20, 2007 (DE) .................... 10 2007 062 440
Apr. 12, 2008 (DE) .................... 10 2008 018 569

(51) Int. Cl.
*A61N 1/00* (2006.01)
(52) U.S. Cl. ................ 607/9; 607/4
(58) Field of Classification Search .......... 607/9, 14
See application file for complete search history.

(56) References Cited

U.S. PATENT DOCUMENTS

| 5,720,295 | A | 2/1998 | Greenhut et al. | |
|---|---|---|---|---|
| 6,295,475 | B1 | 9/2001 | Morgan | |
| 7,225,017 | B1 | 5/2007 | Shelchuk | |
| 7,248,925 | B2 | 7/2007 | Bruhns et al. | |
| 7,274,961 | B1 | 9/2007 | Kroll et al. | |
| 2002/0120303 | A1* | 8/2002 | Levine et al. | 607/14 |
| 2002/0128688 | A1 | 9/2002 | Stoop et al. | |
| 2005/0137630 | A1 | 6/2005 | Ding et al. | |
| 2005/0149137 | A1* | 7/2005 | Chinchoy et al. | 607/25 |
| 2006/0235481 | A1 | 10/2006 | Fogoros et al. | |
| 2008/0109041 | A1* | 5/2008 | de Voir | 607/7 |

FOREIGN PATENT DOCUMENTS

| DE | 10136641 | 2/2003 |
|---|---|---|
| EP | 1393774 | 3/2004 |
| WO | 03/105952 | 12/2003 |

OTHER PUBLICATIONS

German Search Report, dated Dec. 12, 2008, 2 pages.
European Search Report, dated Feb. 10, 2009, 6 pages.

* cited by examiner

*Primary Examiner* — Nicole F Lavert
(74) *Attorney, Agent, or Firm* — ARC IP Law, PC; Joseph J. Mayo

(57) ABSTRACT

An implantable heart stimulator (10), which has a right-atrial sensing unit (62), which is connected or is to be connected to a right-atrial electrode for recording electrical potentials of the myocardium of a right atrium, and is implemented to process electrical signals recorded via the right-atrial electrode, and to detect signal features characterizing a right-atrial stimulation and contraction in the electrical signal recorded via the right-atrial electrode. The heart stimulator (10) additionally has a left-ventricular sensing unit (66), which is connected or is to be connected to a left-ventricular electrode for recording electrical potentials of the myocardium of a left ventricle of a heart and is implemented to process electrical signals recorded via the left-ventricular electrode. The left-ventricular sensing unit (66) is implemented to detect signal features in the electrical signal recorded via the left-ventricular electrode which characterize a left-atrial contraction.

9 Claims, 3 Drawing Sheets

BIVENTRICULAR HEART STIMULATOR

This application takes priority from German Patent Application DE 10 2007 062 440.0, filed 20 Dec. 2007 and German Patent Application DE 10 2008 018 569.8, filed 12 Apr. 2008, the specifications of which are both hereby incorporated herein by reference.

BACKGROUND OF THE INVENTION

1. Field of the Invention

The invention relates to an implantable heart stimulator for the cardiac resynchronization therapy (CRT) of a heart. The heart stimulator may be a cardiac pacemaker or an implantable cardioverter/defibrillator (ICD) or a combination of both, which is capable of stimulating one or both atria and one or both ventricles.

2. Description of the Related Art

A heart stimulator of this type typically has one sensing unit and one stimulation unit in each case for all cardiac atria and ventricles included in its function. These units are each connected via electrode lines to electrodes to be implanted at suitable points in the heart in operation of the heart stimulator. The electrode line having the electrodes for detecting electrical potentials in the right atrium of the heart and for delivering right-atrial stimulation pulses are typically components of an atrial electrode line, for example. The electrodes for detecting electrical potentials in the right ventricle and for delivering right-ventricular stimulation pulses are typically fastened to a right-ventricular electrode line, whose distal end extends up into the apex of the right ventricle. The electrode line having the electrodes for detecting electrical potentials in the left ventricle of the heart and for delivering left-ventricular stimulation pulses is typically a component of a left-ventricular electrode line, which is laid through the coronary sinus of a heart and therefore is also referred to as a coronary sinus electrode line. All electrode lines are typically connected at their proximal end via standardized plug connections to a corresponding heart stimulator.

The typical stimulation modes of a heart stimulator, such as AAI, VVI, VDD, or DDD may be assumed to be known. This is also true for the delivery of stimulation pulses only as needed (demand pacemaker), in which the delivery of a stimulation pulse to the atrium or to the particular ventricles of a heart is suppressed if a particular intrinsic action (intrinsic contraction) of the heart atrium or the heart ventricle was previously detected via an assigned sensing unit of the heart stimulator in a corresponding escape interval. These concepts, which are known per se, may also be implemented in the heart stimulator described here.

For an atrium-synchronous stimulation, in particular in a biventricular DDD stimulation mode, an atrioventricular delay interval (also referred to hereafter as the atrioventricular delay time or as the AV time) which is adapted as well as possible to the individual patients is desirable. The atrioventricular delay time begins with an atrial trigger event and ends with a stimulation of the ventricle. The atrial trigger event may, depending on the current stimulation mode (VDD or DDD stimulation), either be the natural atrial action perceived via an atrial electrode or an atrial stimulus. The atrioventricular delay times are thus determined by two different time intervals, either that for the DDD stimulation or that for the VDD stimulation being active as a function of the current stimulation mode of the pacemaker.

The interatrial conduction time begins in DDD stimulation with the right-atrial stimulus and in DDD stimulation with a signal feature characterizing the right-atrial contraction, and ends in both stimulation modes with an electrical signal feature which characterizes the left-atrial contraction.

The stimulation of the ventricle (ventricular stimulation) typically results in a contraction of the stimulated ventricle, i.e., in a stimulated ventricular event. A ventricular contraction does not occur after ventricular stimulation only if the ventricular is still refractory because of a corresponding contraction occurring shortly beforehand or if the strength of the ventricular stimulation pulse is insufficient (is sub-threshold) to depolarize at least some cells of the ventricular myocardium. A ventricular stimulation pulse is also not even triggered in the so-called demand mode of the heart stimulator if the cardiac pacemaker detects a natural ventricular contraction (a natural ventricular event) within a ventricular escape interval, which is a function of the atrioventricular delay time. In this case, the delivery of the ventricular stimulation pulse is inhibited. All of these may be presumed to be known.

The detection of a contraction is typically performed with the aid of electrodes which record electrical potentials of the myocardium in the particular cardiac area (this refers to the particular atrium or the particular ventricle of a heart) and by a particular sensing unit which analyzes the particular time curve of the recorded potential, and in the simplest case by a threshold value comparison. This is because the potential curve displays typical signal peaks in the case of depolarizations of the myocardium accompanying a contraction of the myocardium in the particular cardiac area.

BRIEF SUMMARY OF THE INVENTION

The heart stimulator affected here is a biventricular heart stimulator which is fundamentally capable of stimulating both ventricles of the heart continuously or on-demand. Biventricular heart stimulators of this type are typically also used for the stimulation of the right atrium on demand, in addition to the stimulation of the two ventricles, and are therefore also referred to as 3-chamber cardiac pacemakers. They are used for a resynchronization therapy known per se, for example (CRT: cardiac resynchronization therapy).

The object of the invention is to provide a biventricular heart stimulator which allows a simple determination of the individual interatrial conduction times for atrial-sensing and atrial-stimulating atrioventricular stimulation and thus makes possible the requirement for a simple optimization of the AV times for VDD and DDD stimulation without additional effort and/or strain for physician and patient.

This object is achieved according to the invention by a heart stimulator of the type cited at the beginning, which has a right-atrial sensing unit, which is connected or is to be connected to a right-atrial electrode for recording electrical potentials of the myocardium of a right atrium of a heart and is implemented to process electrical signals recorded via the right-atrial electrode and to detect signal features in the electrical signal recorded via the right-atrial electrode, which characterize a right-atrial contraction. The heart stimulator additionally has a left-ventricular sensing unit, which is connected or is to be connected to a left-ventricular electrode for recording electrical potentials of the myocardium of a left ventricle of a heart and is implemented to process electrical signals recorded via the left-ventricular electrode. According to the invention, the left-ventricular sensing unit is to detect signal features in the electrical signal recorded via the left-ventricular electrode of a left-atrial depolarization which characterize a left-atrial contraction. In addition, the left-ventricular sensing unit is typically also implemented for the purpose of detecting in a typical way those signal features which characterize a left-ventricular depolarization and thus a contraction of the left ventricle.

The invention provides the advantage that no additional electrode lines are necessary for detecting the occurrence of left-atrial events, but rather only those present in any case in typical biventricular heart stimulators, in particular the left-ventricular electrode line. The invention thus in particular also describes a simple possibility for optimizing the AV times, without the implantation effort being increased. The electrode lines and the particular implant used remain unchanged, only the analysis of the sense signals in the heart stimulator is altered. This represents a great advantage in relation to the configuration known from U.S. Pat. No. 6,295,475, for example.

The right-atrial sensing unit and the left-ventricular sensing unit are preferably connected to a detection unit of the heart stimulator, which is in turn implemented to automatically or manually determine the duration of interatrial conduction times by determining the time difference between the occurrence of a signal feature, either characterizing a right-atrial stimulus or a right-atrial contraction as a function of the operating mode (VDD or DDD stimulation), and the occurrence of a signal feature characterizing a left-atrial contraction to be assigned to one of these events.

The detection unit may also be a component of a programming device, to which the signals to be analyzed are telemetrically transmitted. It may also comprise a combination of functional elements in the cardiac pacemaker and in the programming device.

The detection unit is preferably also implemented to determine the atrioventricular delay intervals for atrial-sensing and atrial-stimulating atrioventricular stimulation on the basis of the interatrial conduction times and possibly further input variables. This may be performed, for example, by addition of an empirically found time interval or in the way known from U.S. Pat. No. 7,248,925.

The left-ventricular sensing unit is preferably also implemented to detect features characterizing both the left-ventricular contraction and also the left-atrial contraction and differentiate them from one another.

This may be performed, for example, on the basis of a double threshold value comparison using two different threshold values. If a peak value in the time curve of the left-ventricular signal simultaneously exceeds a first, lower and a second, higher of two threshold values, the left-ventricular sensing unit detects a left-ventricular event and outputs a corresponding output signal. However, if the peak value in the time curve of the left-ventricular signal only exceeds the first, lower threshold value and not the second, higher of the two threshold values, the left-ventricular sensing unit detects a left-atrial event and outputs a corresponding output signal.

Alternatively thereto, the left-ventricular sensing unit may also be implemented to perform signal features characterizing a particular left-ventricular contraction and a particular left-atrial contraction on the basis of a comparison of morphology features of a particular current signal to stored morphology features. For this purpose, the left-ventricular sensing unit may be implemented to subject a particular signal recorded via the electrode line to a wavelet transformation, to then compare wavelet coefficients thus obtained to stored comparison coefficients. Typical comparison coefficients for a left-atrial contraction and also for a left-ventricular contraction are stored for this purpose in the heart stimulator.

Because in certain circumstances left-atrial signals having very small amplitude are to be expected, the left-ventricular sensing unit may also be implemented in such a way that the moments of the above-mentioned threshold values or morphology features within a stimulation cycle are first determined after summation of a specific number of individual cardiac actions in the meaning of a signal averaging technology.

In each case, the determination of the atrioventricular delay intervals for DDD and VDD stimulation is performed by measuring individual time intervals, which occur between the signal feature characterizing the right-atrial stimulation or contraction and the signal feature, a threshold value, or morphology future to be assigned to the left-atrial contraction.

The measurement of the atrial-ventricular delay intervals may fundamentally be performed both manually and also automatically in the heart stimulator or in the programming device or in the combination of both.

The implantable heart stimulator is preferably a cardiac pacemaker or a cardioverter/defibrillator. Further advantageous embodiments result by combination of the features described here with one another and with those features which are known from the prior art.

BRIEF DESCRIPTION OF THE DRAWINGS

The invention will be explained in greater detail on the basis of an exemplary embodiment with reference to figures. In the figures.

DETAILED DESCRIPTION OF THE INVENTION

Figure 1:
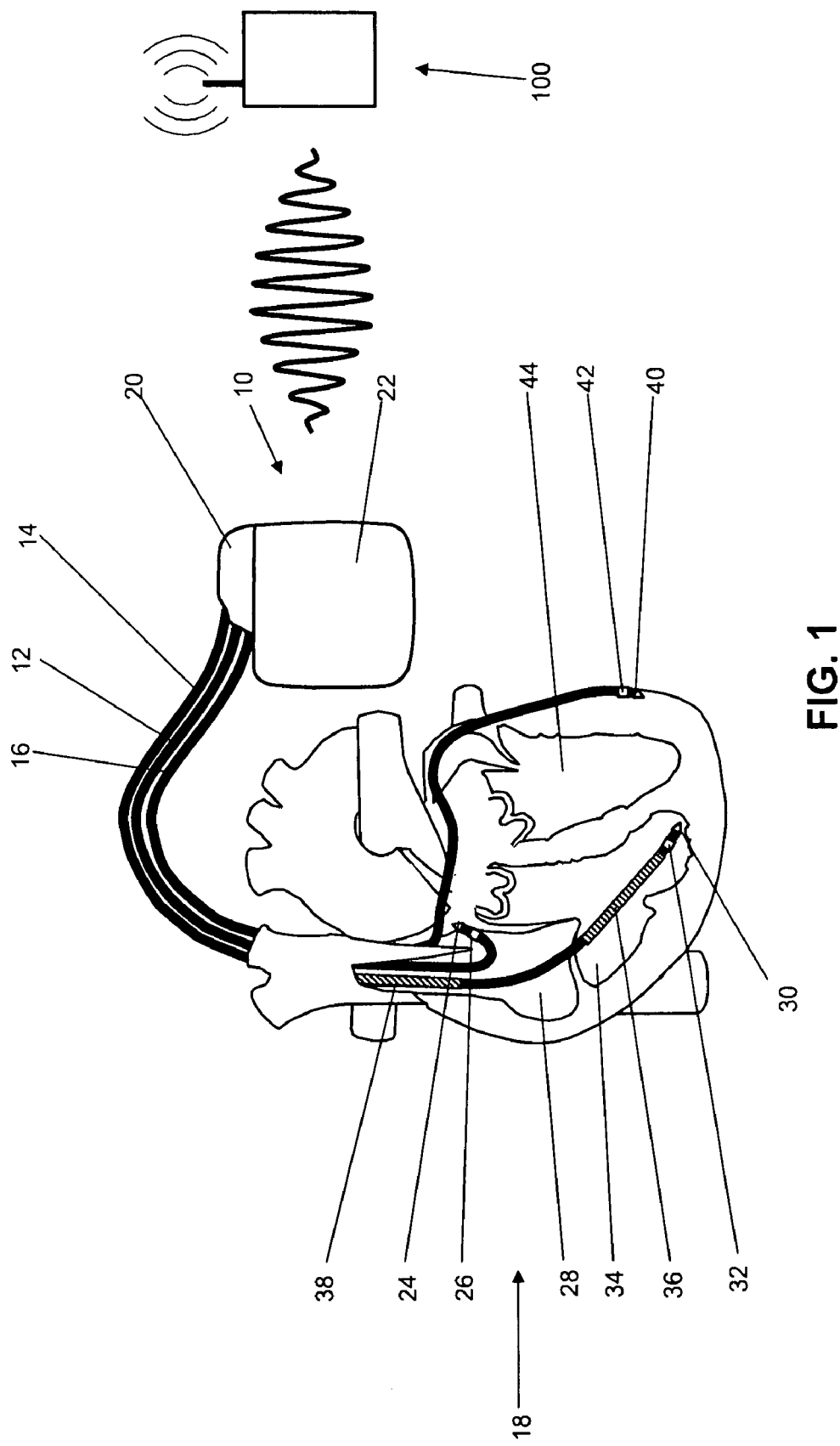
FIG. 1: shows an illustration of a biventricular heart stimulator having connected electrodes situated in the heart.

FIG. 1 shows an implantable heart stimulator 10 in the form of a three-chamber cardiac pacemaker/cardioverter/defibrillator having electrode lines 12, 14, and 16 connected thereto, in connection with a heart 18. In addition, an external device 100 is shown in proximity to the implanted heart stimulator 10. The electrode lines 12, 14, and 16 are electrically connected via known, standardized plug connections to contact sockets in a header (terminal housing) 20 of the heart stimulator 10. In this way, the electrode lines 12, 14, and 16 are also connected to electronic components in the interior of a hermetically sealed metal housing 22 of the heart stimulator 10. These components are schematically shown in greater detail hereafter and determine the mode of operation of the heart stimulator 10 according to the invention.

The electrode line 12 is a right-atrial electrode line and has an atrial tip electrode RA tip 24 on its distal end and, at a short distance therefrom, an atrial ring electrode RA ring 26, which are both placed in the right atrium 28 of the heart 18.

The electrode line 14 is a right-ventricular electrode line and has a right-ventricular tip electrode RV tip 30 on its distal end and, in direct proximity thereto, a right-ventricular ring electrode RV ring 32. Both electrodes are situated in the apex of the right ventricle 34 of the heart 18.

In addition, the right-ventricular electrode line 14 also has a right-ventricular shock coil RV shock 36 as a large-area electrode for delivering relation shocks. A further shock coil 38 is situated in the superior vena cava and is therefore also referred to hereafter as the SVC shock electrode.

The electrode line 16 is a left-ventricular electrode line, on whose distal end a left-ventricular tip electrode LV tip 40 is situated, and, in proximity thereto, a left-ventricular ring electrode LV ring 42. The left-ventricular electrode line 16 is led out from the right atrium 28 of the heart 18 via the coronary sinus into a lateral vein branching therefrom and is therefore also referred to as the coronary sinus electrode line or CS electrode line.

Figure 2:
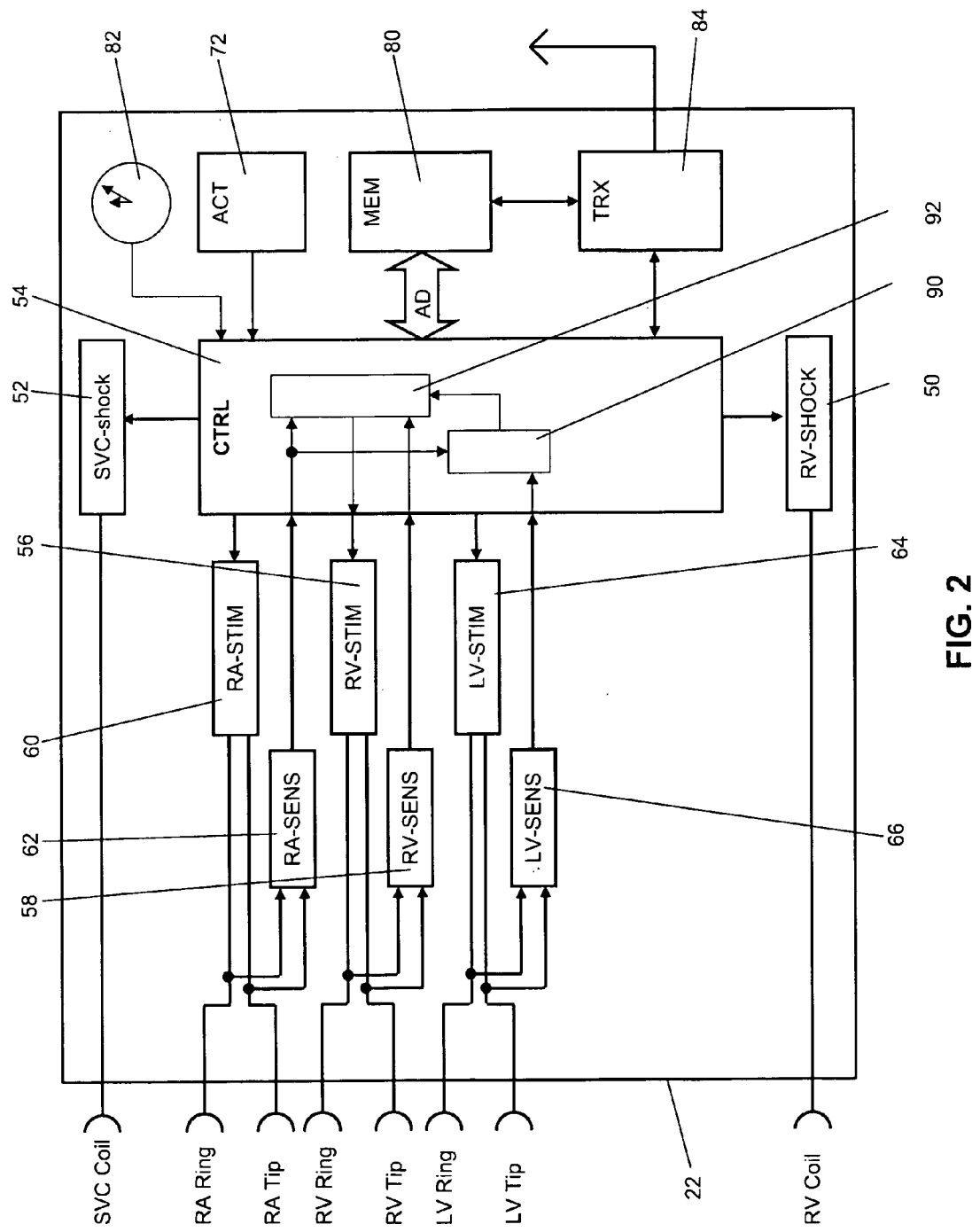
FIG. 2: shows a schematic block diagram of a heart stimulator.

The main components of the heart stimulator 10 are shown in FIG. 2. The electrical terminals for the various electrodes 24, 26, 30, 32, 36, 38, 40, and 42 are shown on the left side. The shock electrodes 36 and 38 are each connected to a right-ventricular shock pulse generator 50 or SVC shock generator 52. Both shock generators 50 and 52 are connected to a stimulation control unit 54, which activates the two shock pulse generators 50 and 52 upon demand to generate and deliver a defibrillation shock.

The terminal for the right-ventricular tip electrode RV tip and the terminal for the right-ventricular ring electrode RV ring are each connected to both a right-ventricular stimulation unit 56 and also a right-ventricular sensing unit 58. Both the right-ventricular stimulation unit 56 and also the right-ventricular sensing unit 58 are connected to the stimulation control unit 54.

The right-ventricular stimulation unit 56 is implemented to generate a right-ventricular stimulation pulse upon an activation signal of the stimulation control unit 54 and deliver it via the terminals of the right-ventricular ring electrode RV ring and the right-ventricular tip electrode RV tip. Alternatively, it is also possible that the housing 22 of the heart stimulator 10 forms a neutral electrode and the right-ventricular stimulation unit 56 is connected to the terminal for the right-ventricular tip electrode RV tip and the housing 22 as the other electrode to deliver a stimulation pulse. A right-ventricular stimulation pulse differs from a defibrillation shock in that the stimulation pulse has a significantly lower pulse strength, so that it does not excite all of the cardiac tissue (myocardium) of a ventricle at once like a defibrillation shock, but rather only the cardiac muscle cells in the immediate surroundings of the right-ventricular tip electrode RV tip 30. This excitation then propagates further via the entire right ventricle 34 by natural stimulation conductance and thus ensures a stimulated contraction of the right ventricle 34.

The right-ventricular sensing unit 58 is implemented to first amplify and filter electrical potentials applied to the terminal for the right-ventricular ring electrode RV ring and the right-ventricular tip electrode RV tip by an input amplifier. Furthermore, the right-ventricular sensing unit 58 is implemented to analyze the curve of the electrical signals applied to its inputs in such a way that the right-ventricular sensing unit 58 independently detects a natural (intrinsic), i.e., independent contraction of the right ventricle 34. This may occur, for example, in that the curve of the signal applied to the inputs of the right-ventricular sensing unit 58 is compared to a threshold value. The greatest amplitude of the signal in the form of the so-called R wave is typically characteristic for a natural contraction of the right ventricle 34, which may be detected by threshold value comparison. The right-ventricular sensing unit 58 then outputs a corresponding output signal indicating a natural contraction of the right ventricle 34 to the stimulation control unit 54.

The terminal for the right-atrial tip electrode RA tip and the terminal for the right-atrial ring electrode RA ring are connected in a similar way to a right-atrial stimulation unit 60 and also to a right-atrial sensing unit 62, which are each in turn connected to the stimulation control unit 54. The right-atrial stimulation unit 60 is implemented to generate stimulation pulses whose strength is sufficient to excite the right-atrial myocardium. The right-atrial stimulation pulses may have a different pulse strength than the right-ventricular stimulation pulses. The right-atrial sensing unit 62 is implemented to detect a so-called P wave from the curve of the differential signal applied to its inputs, which characterizes a natural (intrinsic) contraction of the right atrium 28. If the right-atrial sensing unit 62 detects a corresponding P wave, it generates an output signal and outputs it further to the stimulation control unit 54, which characterizes a natural contraction of the right atrium 28.

In the same way, the terminal for the left-ventricular tip electrode LV tip and the terminal for the left-ventricular ring electrode LV range are connected to a left-ventricular stimulation unit 64 and a left-ventricular sensing unit 66. The left-ventricular stimulation unit 64 and the left-ventricular sensing unit 66 are also connected to the stimulation control unit 54. Both function similarly to the stimulation units 56 and 60 and sensing units 58 and 62 already described.

Figure 3:
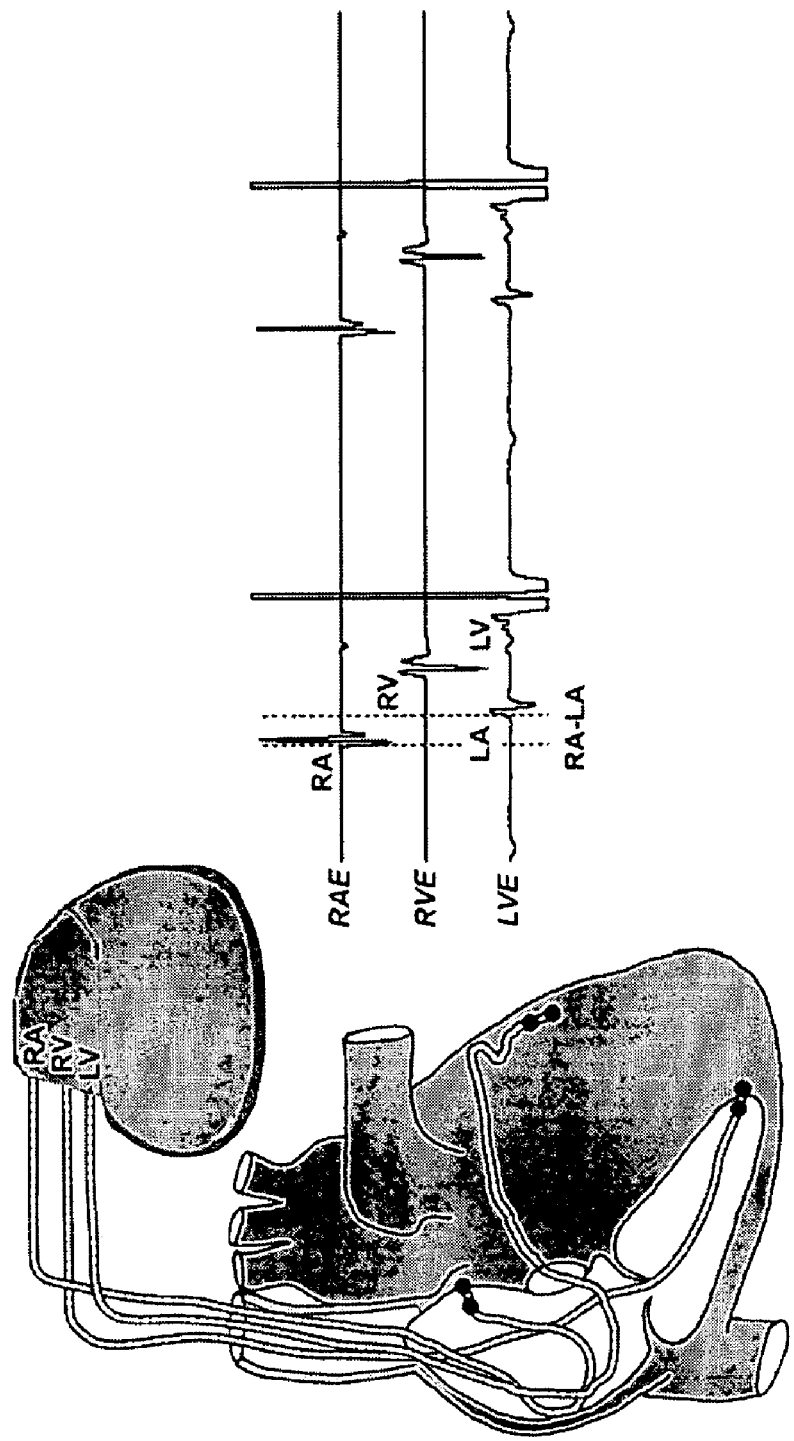
FIG. 3: schematically shows the sensing signals recorded via a particular right-atrial, right-ventricular, and left-ventricular electrode.

In contrast to known left-ventricular sensing units, the left-ventricular sensing unit is implemented to not only detect signal features characterizing a left-ventricular contraction in the recorded electrical signal, but rather also those signal features which characterize a left-atrial contraction, see FIG. 3. Correspondingly, the left-ventricular sensing unit 66 delivers different output signals (markers) for left-ventricular and left-atrial events. The output signals (markers) for left-atrial events are used for one-time or cyclic determination of the duration of interatrial conduction times.

For this purpose, the left-ventricular sensing unit 66 may be implemented so that it performs a double threshold value comparison using two different threshold values. If a peak value in the time curve of the left-ventricular signal simultaneously exceeds a first, lower and a second, higher of two threshold values, the left-ventricular sensing unit detects a left-ventricular event and outputs a corresponding output signal. However, if the peak value in the time curve of the left-ventricular signal only exceeds the first, lower threshold value and not the second, higher of the two threshold values, the left-ventricular sensing unit detects a left-atrial event and outputs a corresponding output signal.

Alternatively thereto, the left-ventricular sensing unit 66 may be implemented to perform signal features characterizing a particular left-ventricular contraction and a particular left-atrial contraction on the basis of a comparison of morphology features of a particular current signal to stored morphology features. For this purpose, the left-ventricular sensing unit 66 subjects the electrical signal recorded via the left-ventricular electrode to a wavelet transformation and subsequently compares wavelet coefficients thus obtained to comparison coefficients stored in a memory 80, to thus possibly detect a particular left-atrial or left-ventricular contraction.

The left-ventricular sensing unit may also be implemented so that the moments of the occurrence of the above-mentioned threshold values or morphology features within the stimulation cycle are first determined after summation of a specific number of individual cardiac actions in the meaning of a signal averaging technique.

As a further component of the heart stimulator 10, an acceleration sensor 72 is connected to the stimulation control unit 54 and integrated in the housing 22 of the heart stimulator 10. The acceleration sensor 72 is implemented to detect a movement signal as a function of the physical activity of a patient and to output a corresponding first accelerometer output signal indicating the physical activity of the patient to the stimulation control unit 54. This allows the stimulation control unit 54 to adapt the timing of the stimulation pulses to the demand of the patient (hemodynamic demand).

Furthermore, the heart stimulator 10 comprises a memory unit 80, which is connected to the stimulation control unit 54 and allows it to store signals generated or analyzed by the stimulation control unit 54. On the other hand, the memory unit 80 allows control programs for the stimulation control unit 54 to be stored in changeable form. Furthermore, the stimulation control unit 54 is connected to a timer 82.

The memory unit 80 is connected to a telemetry unit 84, which allows it to transmit data stored in the memory unit 80 wirelessly to the external device 100 or to transmit programming commands on the part of the external device 100 to the heart stimulator 10 and store them in the memory unit 80.

As a three-chamber heart stimulator/cardioverter/defibrillator, the heart stimulator 10 is capable of performing a stimulation of the right atrium 28, the right ventricle 34, and the left ventricle 44 or also only one or two of these heart chambers in a way known per se. This particularly includes the stimulation of a particular ventricle in the demand mode, in which stimulation pulses are only delivered to the particular ventricle if no intrinsic contraction of the particular ventricle is detected in a preceding particular escape interval on the part of the particular sensing unit. The heart stimulator 10 is thus capable of performing the known right-ventricular stimulation modes such as VVI, VVD, or DDD.

Both the interventricular delay time (VV interval), i.e., the time with which a right stimulation pulse and a left stimulation pulse (if they are not inhibited in the demand mode) follow one another, and also the atrioventricular delay time (AP time) required for the particular stimulation mode (VDD or DDD operation) are significant for the timing of the stimulation pulses in the biventricular stimulation mode, in which both ventricles 34 and 44 of a heart 18 are stimulated. This is in turn ideally set as a function of the particular individual interatrial atrioventricular conduction time caused by the implant.

To determine the implant-related interatrial time intervals for VDD and DDD stimulation, the stimulation control unit 54 has a detection unit 90 according to the invention. This may be connected to the sensing units of arbitrary selectable electrodes or to the pacemaker housing. For example, it may preferably be connected to the right-atrial sensing unit 62 and the left-ventricular sensing unit 66 and is implemented to determine the duration of the interatrial time intervals, in that the detection unit 90 determines the time difference between the occurrence of a signal feature characterizing a right-atrial contraction or stimulation and the occurrence of a signal feature characterizing the occurrence of a left-atrial contraction to be assigned to the right-atrial contraction, i.e., the time difference between two atrial events—namely (depending on the mode of operation) a right-atrial stimulus or a right-atrial contraction and a left-atrial contraction—of a stimulation cycle.

The determination of the duration of the interatrial time intervals may also be performed using the programming device. For this purpose, the electrograms or markers containing corresponding signal features are to be transmitted telemetrically from the pacemaker to the programming device. The detection unit is then a component of the programming device. The measurements are then either performed automatically in the programming device or manually, in that the electrograms or markers are shown on the programmer display screen, frozen, and measured using calipers.

The detection unit may also be swapped out to the external device 100. The heart stimulator 10 is then implemented to transmit the data describing the electrical signal recorded via the left-ventricular electrode telemetrically to the external device 100 using a telemetry unit 84.

The detection unit 90 is connected to an AVD determination unit 92 of the stimulation control unit 54, which determines an individually adapted atrioventricular delay interval (AV interval, AVD) on the basis of the particular interatrial conduction time. This may be performed by addition of an empirically found time interval or as described in U.S. Pat. No. 7,248,925, for example.

As shown as an example in FIG. 2, the AVD determination unit 92 is additionally implemented to trigger the right-ventricular stimulation unit 56 at the end of an AV interval, if it was not previously reset by a right-ventricular sense event detected by the right-ventricular sensing unit 58, so that ventricular stimulations are only delivered if needed.

FIG. 3 shows a scheme of a configuration of right-atrial (RA), right-ventricular (RV), and left-ventricular (LV) sensing and/or stimulating pacemaker or defibrillator electrodes in the heart (left), as well as the right-atrial (RAE), right-ventricular (RVE), and left-ventricular (LVE) electrograms electrocardiographically derived therefrom (right) as the particular sensing signal. The implant-related interatrial conduction time in DDD stimulation is measurable in FIG. 3 as the time interval between the right-atrial and left-atrial deflection. Similarly thereto, the interatrial conduction time in DDD stimulation is measurable as the time interval between the right-atrial stimulus and the left-atrial deflection.

LIST OF REFERENCE NUMERALS

| Reference numeral | meaning |
|---|---|
| 10 | heart stimulator |
| 100 | external device |
| 12 | right-atrial electrode line |
| 14 | right-ventricular electrode line |
| 16 | left-ventricular electrode line |
| 18 | heart |
| 20 | header (terminal housing) |
| 22 | housing |
| 24 | atrial tip electrode RA tip |
| 26 | atrial ring electrode RA ring |
| 28 | right atrium |
| 30 | right-ventricular tip electrode RV tip |
| 32 | right-ventricular ring electrode RV ring |
| 34 | right ventricle |
| 36 | right-ventricular shock coil RV shock |
| 38 | shock coil (SVG shock electrode) |
| 40 | left-ventricular tip electrode LV tip |
| 42 | left-ventricular ring electrode LV ring |
| 44 | left ventricle |
| 50 | right-ventricular shock pulse generator |
| 52 | SVC shock pulse generator |
| 54 | stimulation control unit |
| 56 | right-ventricular stimulation unit |
| 58 | right-ventricular sensing unit |
| 60 | right-atrial stimulation unit |
| 62 | right-atrial sensing unit |
| 64 | left-ventricular stimulation unit |
| 66 | left-ventricular sensing unit |
| 72 | acceleration sensor |
| 80 | memory unit |
| 82 | timer |
| 84 | telemetry unit |
| 90 | detection unit |
| 92 | AVD determination unit |

What is claimed is:

1. An implantable heart stimulator (10) comprising:
a right-atrial sensing unit (62), configured to be connected to a right-atrial electrode that is configured to record electrical potentials of myocardium of a right atrium of a heart and is implemented to process electrical signals recorded via the right-atrial electrode and to detect signal features that characterize a right-atrial contraction;

a left-ventricular sensing unit (66), configured to be connected to a left-ventricular electrode that is configured to directly record the electrical potentials of the myocardium of a left ventricle of the heart and indirectly record electrical potentials of the myocardium of the left atrium of the heart is implemented to process electrical signals recorded via the left-ventricular electrode and to detect signal features that characterize a moment of the left-atrial contraction wherein said implantable heart stimulator is not coupled with a left-atrial electrode in the left atrium of the heart.

2. The implantable heart stimulator (10) according to claim 1, wherein the right-atrial sensing unit (62) and the left-ventricular sensing unit (66) are connected to a detection unit (90), which is implemented to calculate a duration of interatrial conduction times based on a difference between a time of the right-atrial contraction upon atrial stimulation by an occurrence of a right-atrial stimulus and upon atrial sensing by a signal feature that characterizes the right-atrial contraction, and a time of an occurrence of a signal feature that characterizes the left-atrial contraction.

3. The implantable heart stimulator (10) according to claim 2, further comprising an AVD determination unit (92), which is connected to the detection unit (90) and is implemented to determine an atrioventricular delay interval based on at least the interatrial conduction time.

4. The implantable heart stimulator (10) according to claim 1, wherein the left-ventricular sensing unit (66) is implemented to detect features that characterize a particular left-ventricular contraction and a particular left-atrial contraction based on a double threshold value comparison using two different threshold values and differentiate the features from one another.

5. The implantable heart stimulator (10) according to claim 1, wherein the left-ventricular sensing unit (66) is implemented to detect signal features that characterize a particular left-ventricular contraction and a particular left-atrial contraction based on a comparison of morphology features of a particular current signal to stored morphology features.

6. The implantable heart stimulator (10) according to claim 5, wherein the left-ventricular sensing unit (66) is implemented to subject the electrical signals recorded via the left-ventricular electrode to a wavelet transformation and subsequently to compare wavelet coefficients thus obtained to stored comparison coefficients and assign them to a left-atrial contraction or a left-ventricular contraction.

7. The implantable heart stimulator (10) according to claim 5, wherein the left-ventricular sensing unit (66) is implemented to signal average the electrical signals recorded via the left-ventricular electrode over a specific number of cardiac actions and to detect a moment that characterizes the left-atrial contraction from a result of the signal average.

8. A cardiac stimulation system having an implantable heart stimulator (10) according to claim 1, and further comprises:

a telemetry unit (84) that is implemented to transmit data that describes the electrical signals recorded via the left-ventricular electrode telemetrically to an external device (100); and, an external device (100), that is implemented to detect signal features that characterize the left-atrial contraction in the electrical signals recorded via the left-ventricular electrode.

9. A cardiac stimulation system having an implantable heart stimulator (10) according to claim 1, and further comprises:

a telemetry unit (84) that is implemented to transmit data that describes the electrical signals recorded via the left-ventricular electrode telemetrically to an external device (100); and, an external device (100) that is implemented to detect signal features in the electrical signals recorded via the left-ventricular electrode which characterize the moment of the left-atrial contraction and to measure a time interval of the signal features to a signal or signal feature which characterizes the right-atrial stimulus or right-atrial contraction automatically or manually through use of calipers.

* * * * *